(12) United States Patent
Chung et al.

(10) Patent No.: US 9,074,951 B2
(45) Date of Patent: Jul. 7, 2015

(54) BLOOD PROCESSING SYSTEM

(75) Inventors: Terry Chung, Kildeer, IL (US); Kwang Suk Kim, Palatine, IL (US); James Darren Roxas, Chicago, IL (US); David Shao Ling, Vernon Hills, IL (US)

(73) Assignee: Fenwal, Inc., Lake Zurich, IL (US)

( * ) Notice: Subject to any disclaimer, the term of this patent is extended or adjusted under 35 U.S.C. 154(b) by 330 days.

(21) Appl. No.: 13/572,430

(22) Filed: Aug. 10, 2012

(65) Prior Publication Data
US 2013/0036824 A1 Feb. 14, 2013

Related U.S. Application Data

(60) Provisional application No. 61/523,001, filed on Aug. 12, 2011.

(51) Int. Cl.
*G01L 7/00* (2006.01)
*G01L 9/00* (2006.01)
*A61M 1/36* (2006.01)
*G01L 19/00* (2006.01)

(52) U.S. Cl.
CPC ............ *G01L 9/0076* (2013.01); *A61M 1/3639* (2013.01); *A61M 2205/3306* (2013.01); *A61M 2205/3372* (2013.01); *G01L 19/0092* (2013.01)

(58) Field of Classification Search
None
See application file for complete search history.

(56) References Cited

U.S. PATENT DOCUMENTS

| 5,392,653 | A | 2/1995 | Zanger et al. |
|---|---|---|---|
| 5,462,416 | A | 10/1995 | Dennehey et al. |
| 5,656,163 | A | 8/1997 | Brown |
| 6,254,784 | B1 | 7/2001 | Nayak et al. |
| 6,261,065 | B1 | 7/2001 | Nayak et al. |
| 6,348,156 | B1 | 2/2002 | Vishnoi et al. |
| 6,764,460 | B2 | 7/2004 | Dolecek et al. |
| 7,661,294 | B2 * | 2/2010 | Dam ............................ 73/19.03 |
| 7,847,276 | B2 * | 12/2010 | Carlisle et al. ................ 250/573 |
| 8,176,790 | B2 * | 5/2012 | Birch et al. ...................... 73/705 |
| 2005/0285025 | A1 * | 12/2005 | Boukhny et al. ............ 250/231.1 |
| 2010/0298725 | A1 * | 11/2010 | Vivenzio et al. ............. 600/490 |
| 2011/0130627 | A1 * | 6/2011 | Mcgrail et al. ............... 600/109 |
| 2011/0223581 | A1 * | 9/2011 | Stobbe ............................. 435/3 |
| 2012/0059267 | A1 * | 3/2012 | Lamego et al. ............... 600/483 |

* cited by examiner

*Primary Examiner* — Peter Macchiarolo
*Assistant Examiner* — Jermaine Jenkins
(74) *Attorney, Agent, or Firm* — Foley & Lardner LLP

(57) ABSTRACT

A pressure sensor has a housing, a movable member and a vision sensor. The housing has an aperture configured to receive a fluid. The movable member is disposed in the housing and configured to move in response to a pressure of the fluid. The vision sensor is configured to detect the movement of the movable member.

15 Claims, 7 Drawing Sheets

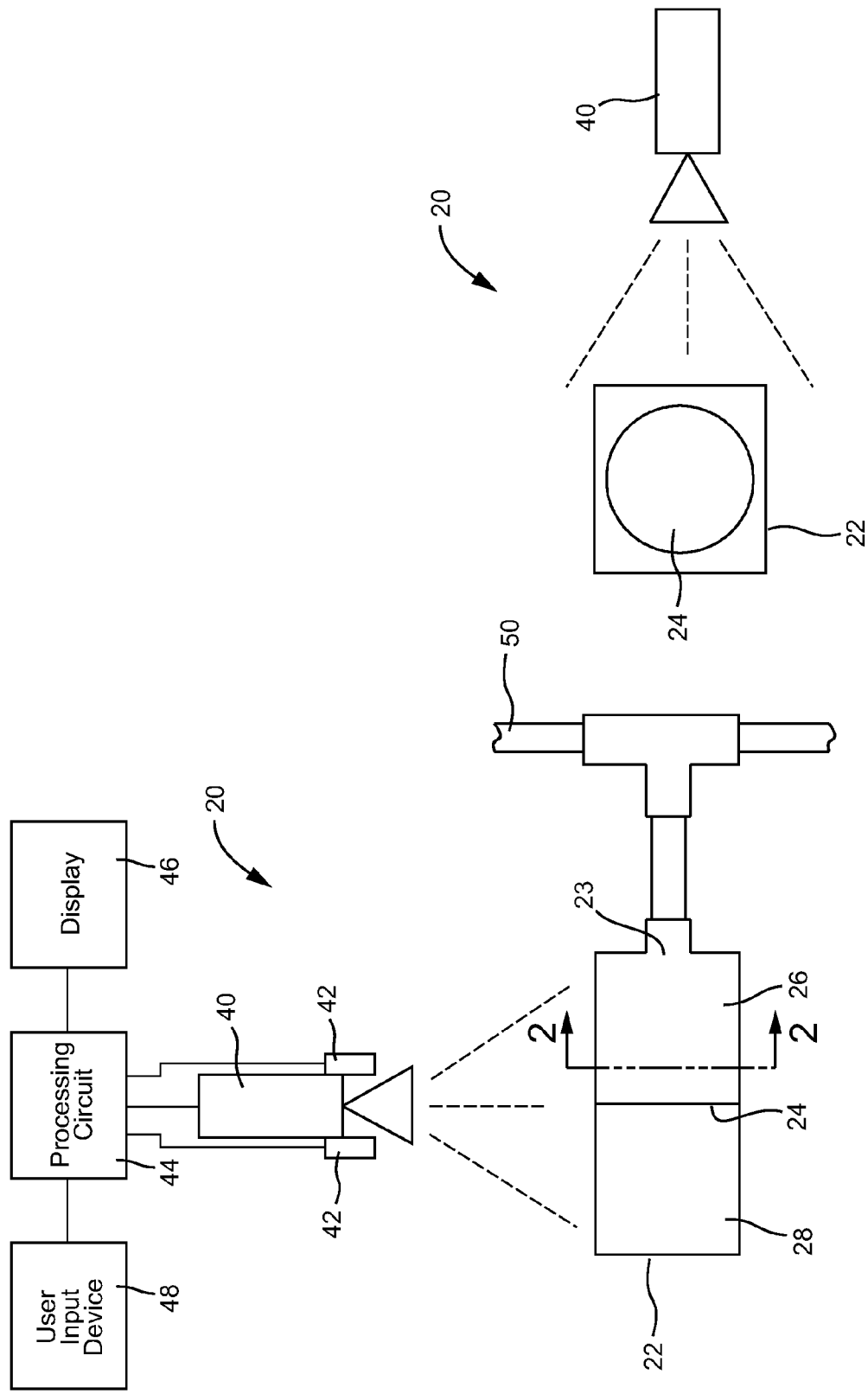

BLOOD PROCESSING SYSTEM

CROSS-REFERENCE TO RELATED APPLICATIONS

This application claims the benefit of U.S. Provisional Application No. 61/523,001 filed Aug. 12, 2011, which is incorporated by reference herein in its entirety.

BACKGROUND

The present invention relates generally to a pressure sensor for a fluid (e.g., a gas or liquid). A wide variety of mechanisms may be used to detect the pressure of a fluid, including a piezoelectric mechanism, a potentiometer, an electromagnetic mechanism, a capacitor, or a piezoresistive mechanism.

In some applications, a disposable pressure sensor may be utilized. For example, a pressure sensor may be utilized in a machine that handles blood, such as a centrifuge that separates blood into its various therapeutic components, (e.g., red blood cells, platelets, plasma, etc.).

It would be advantageous to provide an improved disposable pressure sensor.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

FIG. 1 is a side view of a pressure sensor in an initial or calibration state, according to an exemplary embodiment.

FIG. 2 is a cross-section view of the pressure sensor of FIG. 1 taken along line 2-2, according to an exemplary embodiment.

DETAILED DESCRIPTION

Figure 3:
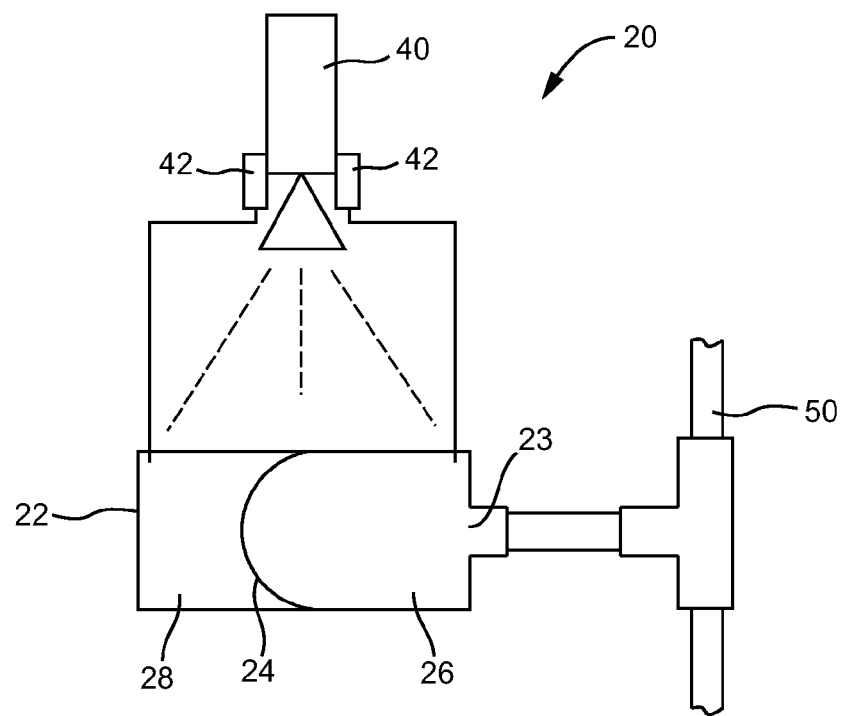
FIG. 3 is a side view of the pressure sensor of FIG. 1 in a positive pressure-sensing state, according to an exemplary embodiment.
Figure 4:
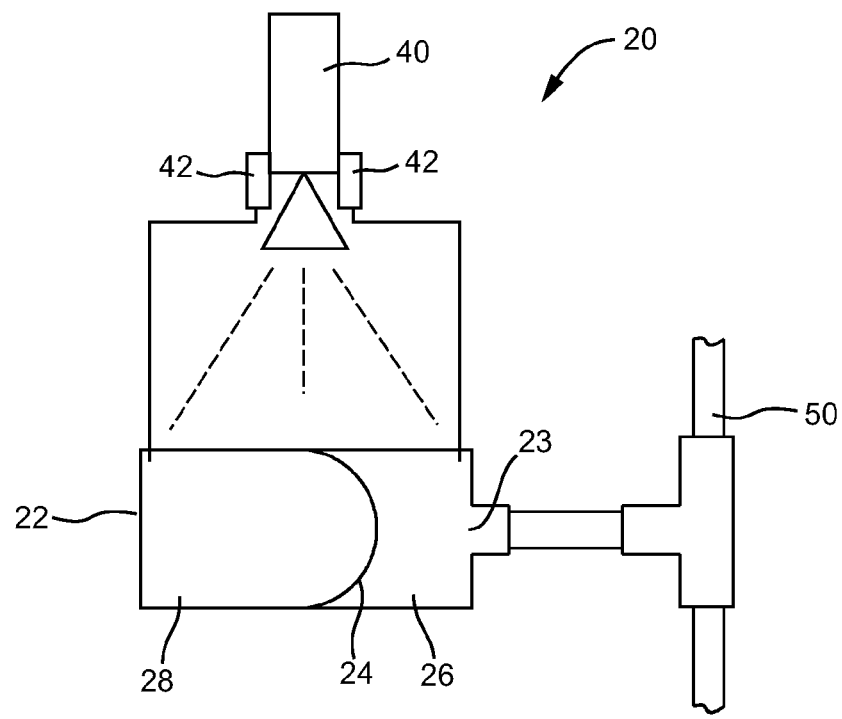
FIG. 4 is a side view of the pressure sensor of FIG. 1 in a negative pressure-sensing state, according to an exemplary embodiment.

It is to be understood that the following detailed description is exemplary and explanatory only, and is not restrictive of the invention as claimed.

Referring to FIGS. 1-4, one exemplary embodiment relates to a sensor 20. The sensor 20 is configured to monitor the pressure of a fluid. Sensor 20 may be utilized as a part of a larger system. Sensor 20 includes a generally hollow housing 22 with an aperture 23 configured to receive a fluid. The fluid may be contained in a fluid system 50. A movable member 24 is disposed in the housing, separating the interior of the housing into a first chamber 26 in fluid communication with aperture 23 and a second chamber 28. According to one exemplary embodiment, a periphery of movable member 24 may be coupled to the interior of housing 22. According to another exemplary embodiment, the interior of housing 22 may be separated into first chamber 26 and second chamber 28 by a stationary rigid wall. Movable member 24 is configured to move in response to a pressure of the fluid admitted into first chamber 26 through aperture 23.

According to one exemplary embodiment, movable member 24 is a flexible membrane or film that is formed from an elastomeric or other flexible material. In one embodiment, the membrane is made from a flexible material that does not yield and remains flexible. Pressure exerted on the membrane forces the membrane to deform relative to a base configuration in which an equal pressure is being exerted on the membrane from first chamber 26 and second chamber 28. If the pressure in first chamber 26 is less than the pressure in second chamber 28 (e.g., a vacuum or negative pressure in fluid system 50), the membrane is deformed into first chamber 26. If the pressure in first chamber 26 is greater than the pressure in second chamber 28 (e.g., a positive pressure in fluid system 50), the membrane is deformed into second chamber 28. The magnitude of the pressure in fluid system 50 (e.g., the pressure differential between first chamber 26 and second chamber 28) is proportional to the relative deformation or displacement of movable member 24.

In other exemplary embodiments, movable member 24 may be a relatively rigid device, such as a shuttle, rigid capsule, or a ball bearing that is confined, for example, by a track or tube in fluid communication with first chamber 26 and second chamber 28. A rigid movable member 24 may be configured to move back and forth along the track or tube in response to a pressure differential between first chamber 26 and second chamber 28.

Housing 22 includes a transparent portion to allow movable member 24 to be visible from outside housing 22. The deformation or displacement of movable member 24 is detected and monitored by a vision or optical sensor 40 (e.g., a camera, a CCD line sensor, a pin diode detector, a multidimensional sensor or array, etc). Vision sensor 40 captures images of movable member 24 that may be analyzed by a computer or other device to detect changes in position of movable member 24 (e.g., deflection, deformation, distortion, translation, etc.) to determine the pressure of fluid system 50. Vision sensor 40 is positioned and may have a field of vision wide enough that is able to capture the full range of motion of movable member 24 or may alternatively capture only a portion of the range of motion of the movable member.

According to an exemplary embodiment, sensor 20 further includes a temperature sensor 42, such as a laser thermocouple or another temperature sensor that is capable of non-contact or non-invasive temperature readings. Temperature sensor 42 monitors the temperature in first chamber 26 and/or second chamber 28 so that sensor 20 can compensate for temperature differences when calculating the pressure of fluid system 50.

Figure 5:
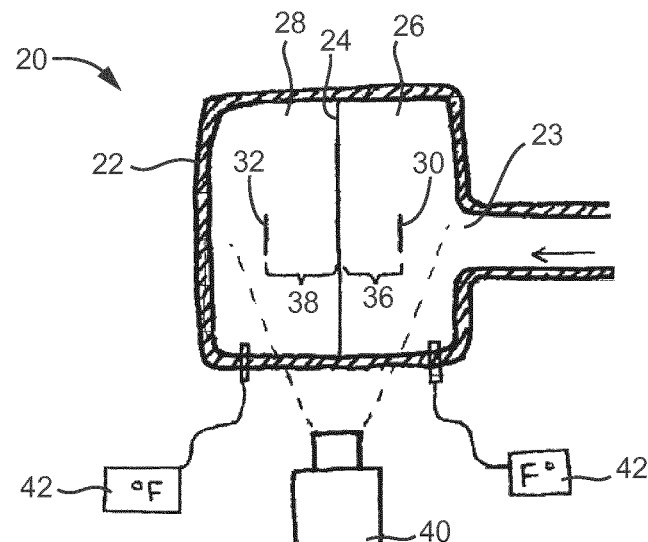
FIG. 5 is a side view of a pressure sensor in an initial or calibration state showing elements for calculating displacement, according to an exemplary embodiment.
Figure 6:
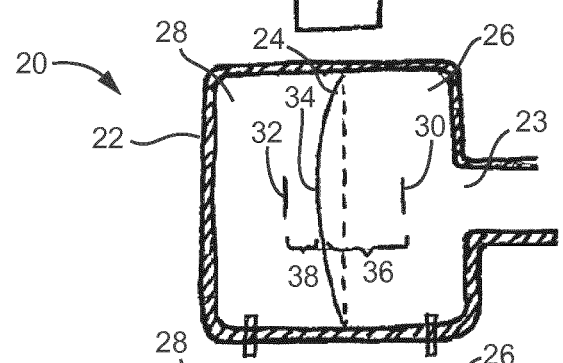
FIG. 6 is a side view of the pressure sensor of FIG. 5 in a positive pressure-sensing state, according to an exemplary embodiment.
Figure 7:
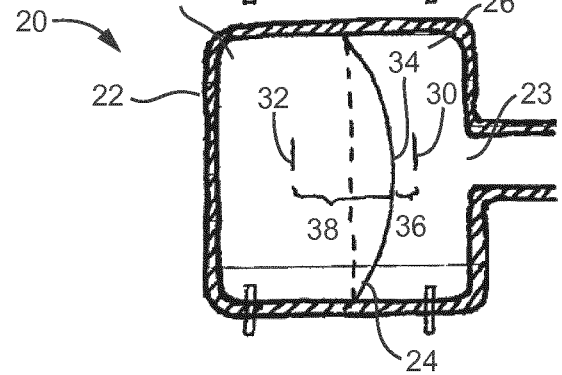
FIG. 7 is a side view of the pressure sensor of FIG. 5 in a negative pressure-sensing state, according to an exemplary embodiment.

Referring to FIGS. 5-7, a sensor 20 is shown according to another exemplary embodiment. Vision sensor 40 may monitor displacement of movable member 24 relative to one or more reference marks 30 and 32. According to one embodiment, a first reference mark 30 may be provided in first chamber 26 and a second reference mark 32 may be provided in second chamber 28. According to another exemplary embodiment, first reference mark 30 and/or second reference mark 32 may be formed on the exterior of housing 22, on a transparent portion of housing such as a window, or at another location of sensor 20.

Vision sensor 40 may capture an image when sensor 20 is coupled to an open fluid system 50. This image and/or data about the image may then be stored and utilized as a zero condition (e.g., base position, reference position, etc.). Vision sensor 40 may utilize a first distance 36 between the peak point 34 of movable member 24 and first reference mark 30 and/or a second distance 38 between peak point 34 and second reference mark 32 to determine the displacement of movable member 24. If the pressure in first chamber 26 is equal to the pressure in second chamber 28, peak point 34 may be an equal distance from first reference mark 30 and second reference mark 32. If the pressures in first chamber 26 and second chamber 28 are not equal, peak point 34 may be closer to first reference mark 30 or second reference mark 32 as the zero condition. In one embodiment, sensor 40 is coupled to a processing circuit which is configured to take a reference point for the zero condition and detect any deflection on either side of the diaphragm to represent a change from the zero condition.

Measurements of fluid pressure in fluid system 50 may be determined by analyzing the difference in position of peak point 34 from the zero condition position. If a negative pressure is present in fluid system 50, peak point 34 will move closer to first reference mark 30, resulting in first distance 36 decreasing and second distance 38 increasing. If a positive pressure is present in fluid system 50, peak point will move closer to second reference mark 32, resulting in first distance 36 increasing and second distance 38 decreasing. In various embodiments, the displacement of movable member 24 and the pressure in fluid system 50 may be determined by analyzing the difference in first distance 36, second distance 38, or a ratio of first distance 36 and second distance 38.

Vision sensor 40 provides a flexible manner of establishing a zero condition and measuring the displacement of movable member 24. Sensor 20 is automatically calibrated with vision sensor 40. Unlike sensors with a mechanical interconnection, sensor 20 does not have to be physically coupled with vision sensor 40 or precisely aligned with vision sensor 40. Vision sensor 40 can record a zero condition and compensate if housing 22 moves, or if movable member 24 is displaced because of an initial or preconditioned pressure difference. Such a preconditioned pressure difference may be the result of, for example, shipping, environmental changes, or previous usage.

As shown in FIG. 1, vision sensor 40 of sensor 20 may be coupled to a processing circuit 44. Processing circuit 44 is configured to calculate the pressure of fluid system 50 based on signals received from the vision sensor 40 and temperature sensors 42. Processing sensor 44 may further be coupled to a display 46 to output the calculated pressure readings to a user. A user input device 48 may be provided to allow a user to interact with sensor 20 (e.g., by performing diagnostic tests, establishing a reference or zero condition, etc.).

Figure 8:
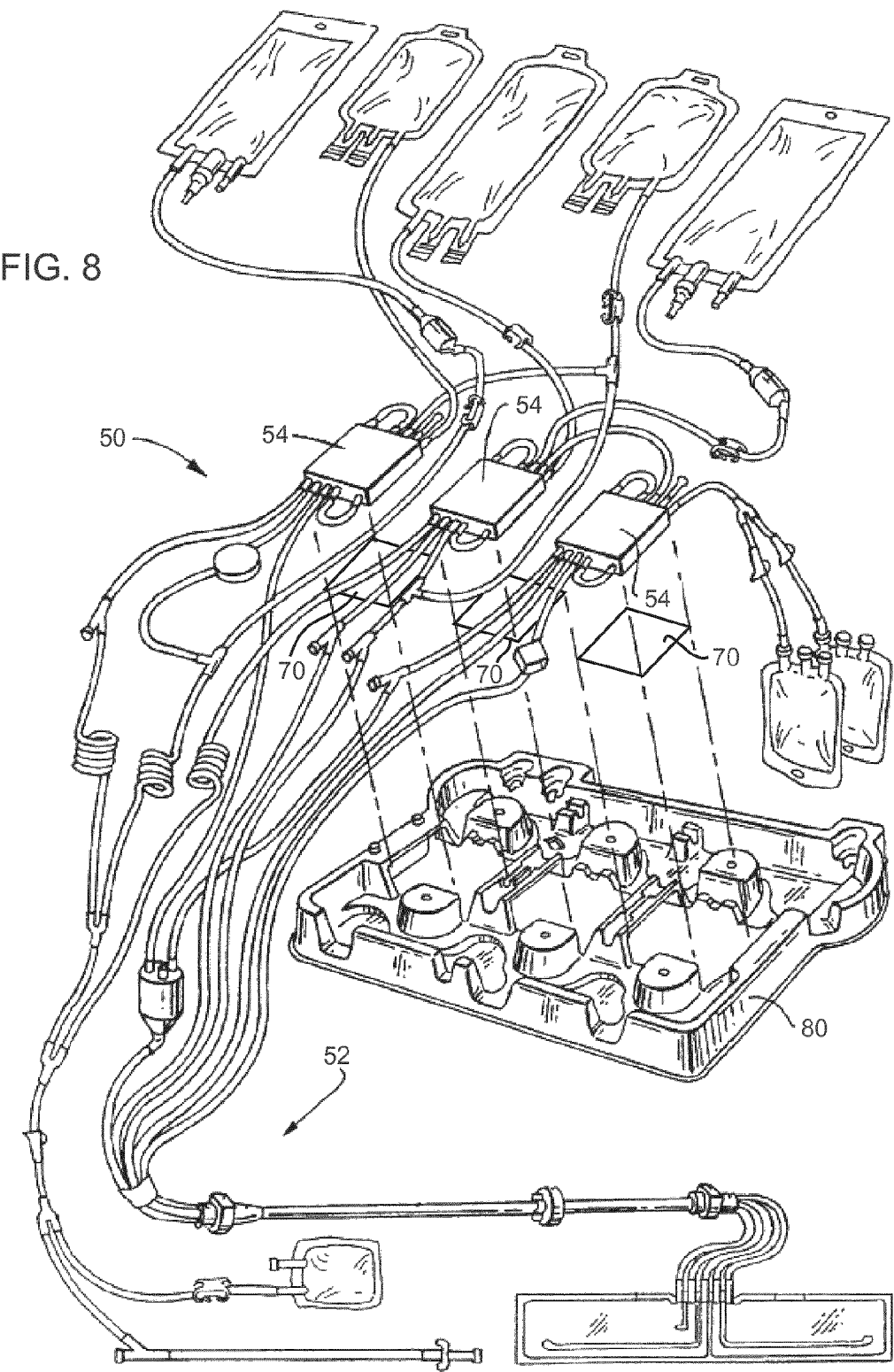
FIG. 8 is an exploded view of a disposable fluid processing assembly usable in association with a centrifuge assembly.

Referring now to FIG. 8, according to one exemplary embodiment, fluid system 50 may be utilized in a blood processing system to process whole blood or other suspensions of biological material. To avoid cross-contamination between patients, the blood processing system may include a first portion or housing configured to be reused for multiple blood processing operations for different patients, and a second portion or housing configured for a single blood processing operation. According to one exemplary embodiment, the first portion may be a device such as a centrifuge and the second portion may be a disposable fluid system 50 (e.g., a fluid processing assembly). Fluid system 50 is insertable to and removable from the centrifuge. Fluid system 50 includes conduits 52 configured to convey fluid through fluid system to and from the centrifuge or other mechanism. Fluid system 50 further includes one or more cassettes 54 that direct liquid flow among multiple fluid sources and destinations during a fluid processing procedure. A movable member 24 is disposed in the cassettes 54. As described above, movable member 24 is configured to move in response to a change in pressure of the blood in fluid system 50.

Figure 9:
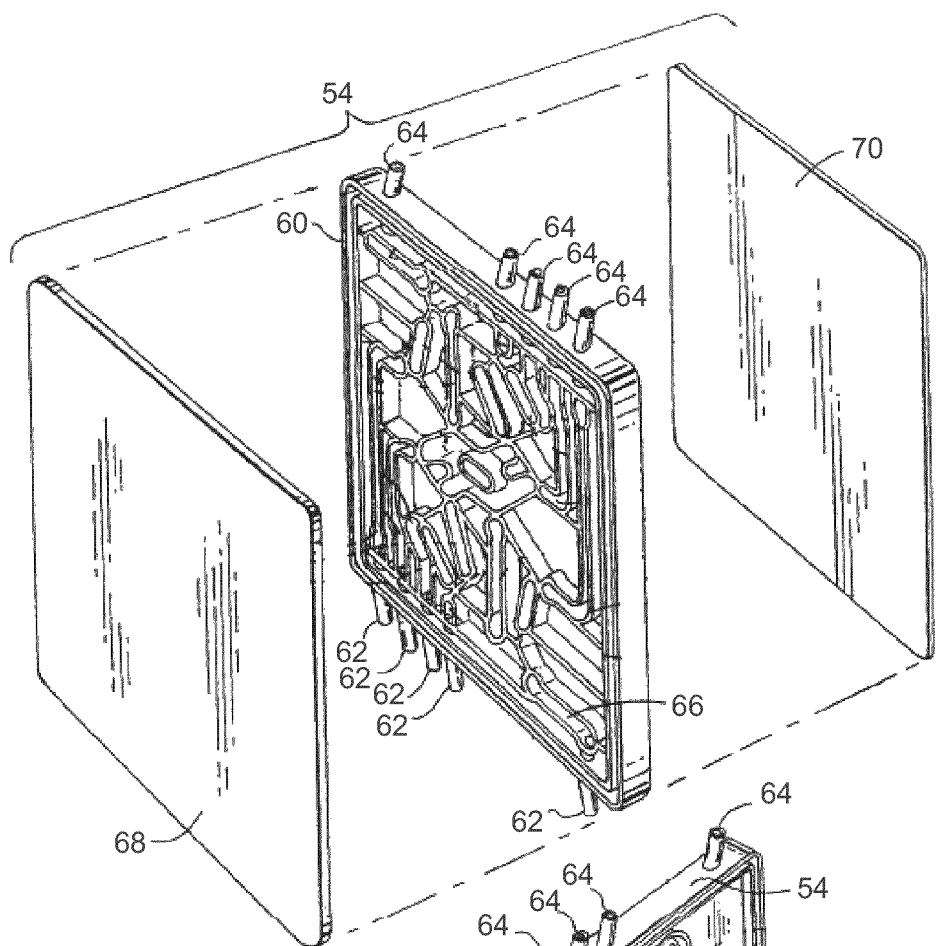
FIG. 9 is a rear isometric exploded view of a fluid control cassette that may be incorporated by the fluid processing assembly of FIG. 8.
Figure 10:
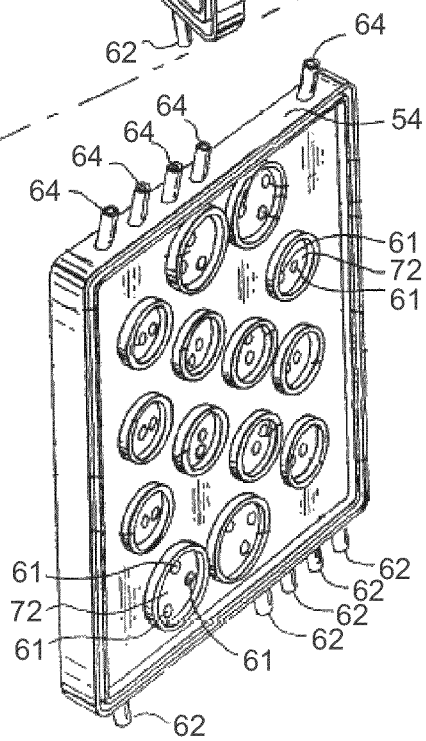
FIG. 10 is a front isometric view of the fluid control cassette of FIG. 9.

As shown in more detail in FIGS. 9 and 10, cassettes 54 have a body or housing 60 that is formed to include one or more input ports 62, one or more output ports 64, and channels 66 that direct fluid from inputs 62 to outputs 64. A cover or panel 68 is coupled to one side of housing 60 while a flexible diaphragm or membrane 70 is coupled to the opposite side of housing 60.

Housing 60 further forms one or more open-ended sensing portions 72. Sensing portions 72 are analogous to first chamber 26 of sensor 20 described above. Apertures 61 in housing 60 allow sensing portions 68 to be in fluid communication with channels 66. The open end of each sensing portion 68 is sealed by membrane 70 (e.g., with an ultrasonic welding operation, a vacuum, etc.). In this way, membrane 70 serves the same function as movable member 24 of sensor 20 described above.

Figure 11:
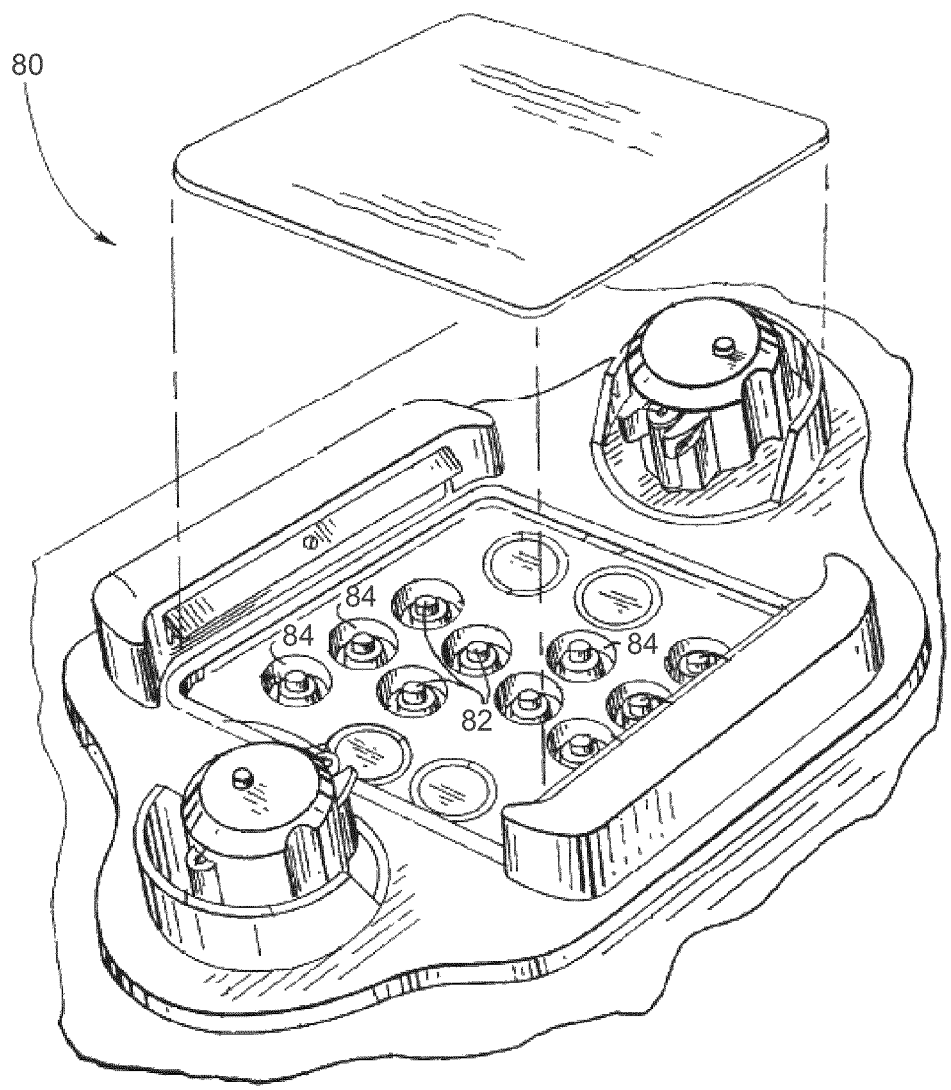
FIG. 11 is an isometric view of a cassette holding station for a centrifuge, according to an exemplary embodiment.

Referring now to FIG. 11, each cassette 54 is received in a holder 80 in the centrifuge. Holder 80 may include actuators 82 that interact with aligned valves in cassettes 54, and vision sensors to sense the displacement of membrane 70 proximate to sensing portions 72. Vision sensors may be provided adjacent to chambers 84 (e.g., hollows, recesses, cavities, etc.) formed in holder 80 that are aligned with sensing portions 72 of cassette 54. Chambers 84 in holder 80 may therefore be analogous to second chamber 28 of sensor 20 described above. Vision sensors may be mounted perpendicular to the moving diaphragm or sheeting for optimal deflection. In the case of an apheresis machine as shown partially in FIG. 11, the camera lens can be installed in a boss from a top panel of the machine. The vision sensor would be focused onto the side of the cassette to monitor deflection of the film.

Once cassette 54 is inserted into holder 80, the vision sensor may capture an image of membrane 70 to establish a reference or zero condition. Cassette 54 includes a transparent portion proximate to each sensor portion 72 to allow the vision sensor to monitor membrane 70. The position of membrane 70 may be calculated relative to reference marks provided on holder 80 and/or cassette 54. As a fluid such as blood flows through channels 66 in cassette 54, the displacement of portions of membrane 70 are monitored. The vision sensor may then generate a signal indicative of the movement and transmit the signal to a processing circuit coupled to the vision system configured to calculate a pressure of the blood in various channels 66. This data may be used for various other processes associated with the blood processing system, such as operating valves in cassettes 54 using actuators. Holder 80 may further collect temperature data using non-contact temperature sensors as described above.

Figure 12:
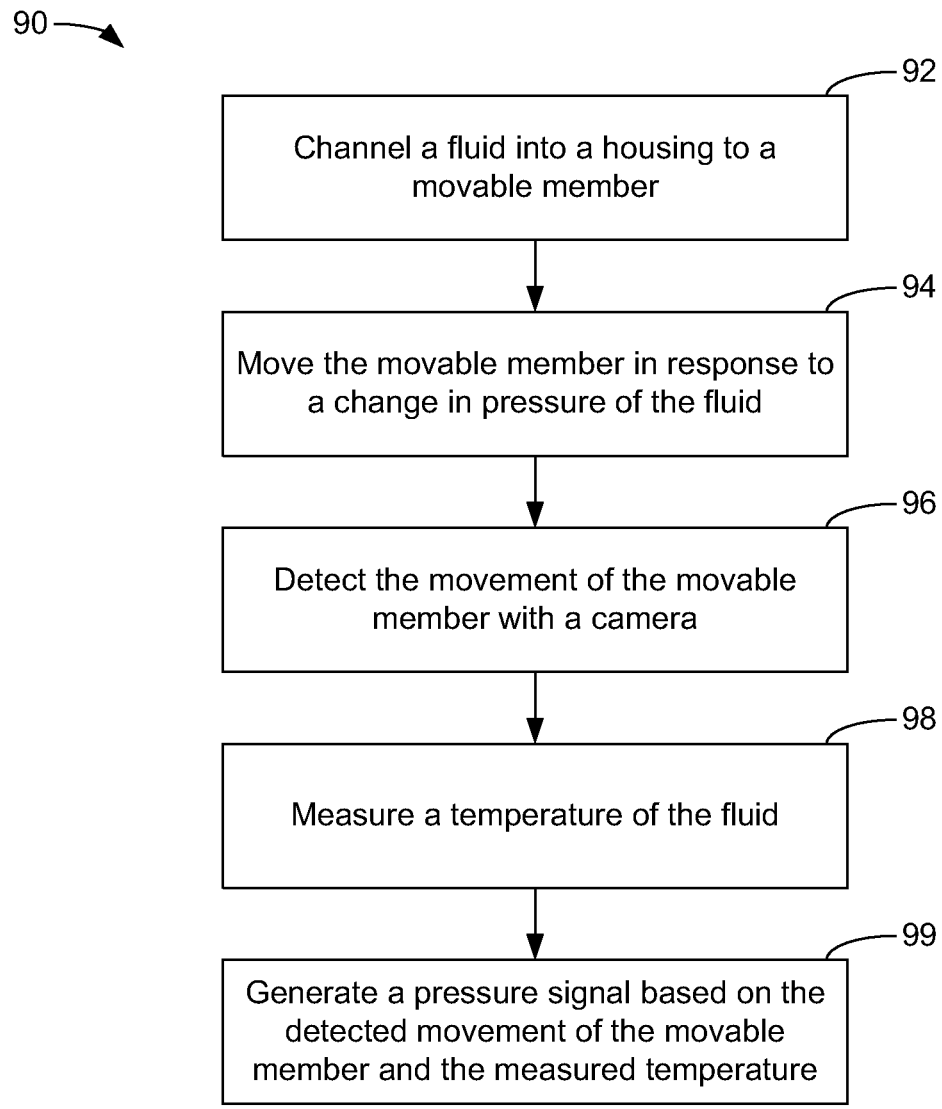
FIG. 12 is a flowchart of a method for measuring the pressure of a fluid, according to an exemplary embodiment.

Referring to FIG. 12, a flowchart of a method 90 for measuring the pressure of a fluid is shown according to an exemplary embodiment. A fluid is first channeled into a housing to a movable member (step 92). The movable member is displaced or deformed in response to a change in pressure of the fluid (step 94). The movable member may be a flexible member that is moved in a first direction in response to an increase in pressure in the fluid and moved in a second direction opposite the first direction in response to a decrease in pressure of the fluid. The displacement or deformation of the movable member is detected with a camera or other vision sensor (step 96). The displacement of the movable member may be detected, for example, through a transparent portion of a housing within which the movable member is disposed.

The temperature of the fluid may be measured (step 98). A pressure signal may be generated based on the detected movement of the movable member and the measured temperature of the fluid (step 99).

Some embodiments may provide for noninvasive, extracorporeal pressure monitoring of a fluid, such as blood. Monitored pressure data may be utilized to facilitate the processing of the fluid, such as the separation of blood into its component parts.

Some embodiments may provide a low cost pressure sensor for systems in which some of the system is configured to be disposable. As described, sensor 20 is configured to include a portion interacting with the fluid (e.g., housing 22 and movable member 24) that is relatively low cost that separates from a second portion that includes more expensive components (e.g., vision sensor 40, temperature sensors 42, etc.). The lower cost components may then be disposed of after each use while the more expensive components are retained to be used multiple times.

Some embodiments may provide a pressure sensor with a disposable portion and a non-disposable portion that do not require physical coupling or precise positioning to function correctly. In this way, the installation of a new disposable portion may be accomplished quickly and easily without negatively effecting the accuracy of data collected with the pressure sensor.

Some embodiments may provide a mechanism for sensing pressure that can easily compensate for environmental variations and physical misalignments by providing an adaptable system for establishing a reference or zero condition.

The construction and arrangement of the elements of the pressure sensor as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. Some like components have been described in the present disclosure using the same reference numerals in different figures (e.g., housing 22). This should not be construed as an implication that these components are identical in all embodiments; various modifications may be made in various different embodiments. It should be noted that the elements and/or assemblies of the enclosure may be constructed from any of a wide variety of materials that provide sufficient strength or durability, in any of a wide variety of colors, textures, and combinations. The processing circuit may comprise any digital and/or analog circuit components configured to perform the functions recited herein. The processing circuit may comprise one or more modules, units, circuits, etc., may comprise a microprocessor, microcontroller, application-specific integrated circuit, programmable logic, or other circuitry. The processing circuit may comprise a tangible computer-readable memory having instructions encoded thereon which when processed by a processor perform the functions recited herein. Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present inventions. Other substitutions, modifications, changes, and omissions may be made in the design, operating conditions, and arrangement of the preferred and other exemplary embodiments without departing from the spirit of the appended claims.

What is claimed is:

1. A blood processing system, comprising:
   a first housing configured to be reused for multiple blood processing operations for different patients;
   a second housing configured for a single blood processing operation, the second housing insertable to and removable from the first housing, the second housing comprising a conduit configured to house blood and a pressure sensing portion having a movable member disposed therein, the movable member configured to move in response to a change in pressure of the blood; and
   a vision system coupled to the first housing and configured to be reused for multiple blood processing operations, the vision system configured to detect movement of the movable member and to generate a signal indicative of the movement.

2. The blood processing system of claim 1, further comprising a processing circuit coupled to the vision system configured to calculate a pressure of the blood based on the signal indicative of the movement.

3. The blood processing system of claim 2, further comprising a display to output the pressure.

4. The blood processing system of claim 2, wherein the processing circuit is configured to control operation of an actuator in order to operate a valve in the second housing based on the signal indicative of the movement.

5. The blood processing system of claim 1, wherein the second housing is part of a cassette comprising an input port, an output port, and channels including the conduit, the second housing further comprising a substantially transparent portion in the vicinity of the vision system when the second housing is disposed in the first housing.

6. The blood processing system of claim 1, wherein the second housing is disposable.

7. The blood processing system of claim 1, further comprising a temperature sensor configured to measure a temperature of the fluid and a processing circuit configured to calculate a pressure based on the signal indicative of the movement and signals from the temperature sensor.

8. The blood processing system of claim 7, wherein the temperature sensor comprises a laser thermosensor.

9. The blood processing system of claim 1, wherein the first housing comprises a centrifuge.

10. The blood processing system of claim 1, wherein the second housing comprises a fluid processing assembly.

11. The blood processing system of claim 1, further comprising a user input device.

12. The blood processing system of claim 11, wherein the user input device is configured to enable a user to interact with the blood processing system.

13. The blood processing system of claim 12, wherein the user input device is configured to enable a user to perform at least one of performing a diagnostic test and establishing a reference condition.

14. The blood processing system of claim 1, wherein the vision system comprises a vision sensor mounted perpendicular to the movable member.

15. The blood processing system of claim 1, wherein the vision system is configured to store image data comprising an image regarding the movable member.

\* \* \* \* \*